United States Patent [19]

Swenson

[11] Patent Number: 4,581,024

[45] Date of Patent: Apr. 8, 1986

[54] NEEDLE ASSEMBLY

[75] Inventor: Jon D. Swenson, Wayne, N.J.

[73] Assignee: Becton, Dickinson and Company, Paramus, N.J.

[21] Appl. No.: 679,847

[22] Filed: Dec. 10, 1984

[51] Int. Cl.$^4$ ............................................. A61M 5/325
[52] U.S. Cl. ..................................... 604/240; 604/272
[58] Field of Search ............... 604/272, 241, 242, 243, 604/240, 263

[56] References Cited

U.S. PATENT DOCUMENTS

| | | | |
|---|---|---|---|
| 2,806,473 | 9/1957 | Lingley | 604/243 |
| 3,035,616 | 5/1962 | Hamilton | 604/243 X |
| 3,186,408 | 6/1965 | Jacob | 604/240 |
| 3,372,697 | 3/1968 | Keller | 604/241 |
| 3,523,532 | 8/1970 | Burke | 604/243 |

Primary Examiner—John D. Yasko
Attorney, Agent, or Firm—John L. Voellmicke

[57] ABSTRACT

A needle assembly includes a cannula having a lumen therethrough along its longitudinal axis and a hub having a distal end, a proximal end and a passageway therethrough defining a hub longitudinal axis. The cannula is positioned partially within the hub projecting outwardly from the distal end so that the lumen and the passageway are in fluid communication. The proximal end of the hub is adapted to engage and become in fluid communication with the fluid transfer apparatus. A first portion of the passageway at the distal end of the hub contains a quantity of adhesive which contacts the cannula for preventing removal of the cannula from the hub. A second portion of the passageway, adjacent to the first portion, contains a portion of the cannula for limiting angular misalignment between the cannula longitudinal axis and the hub longitudinal axis and for limiting the length of the cannula in the passageway.

20 Claims, 9 Drawing Figures

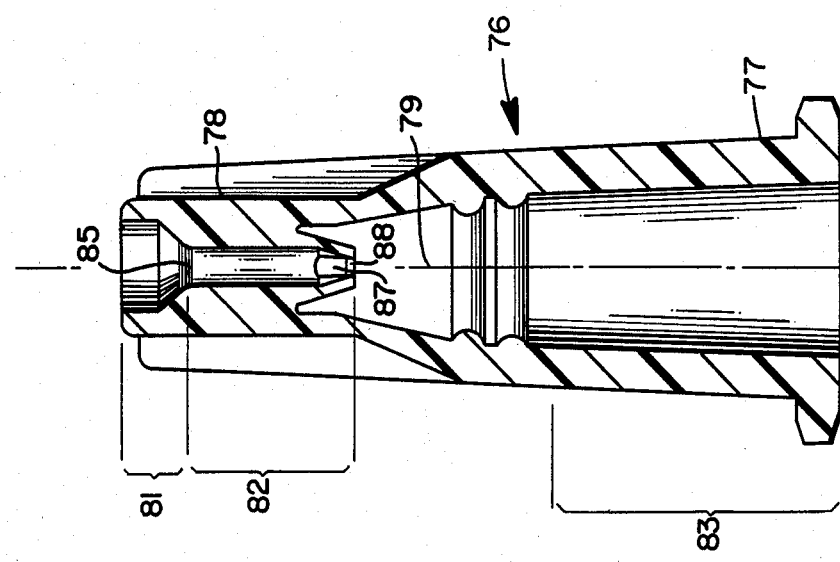
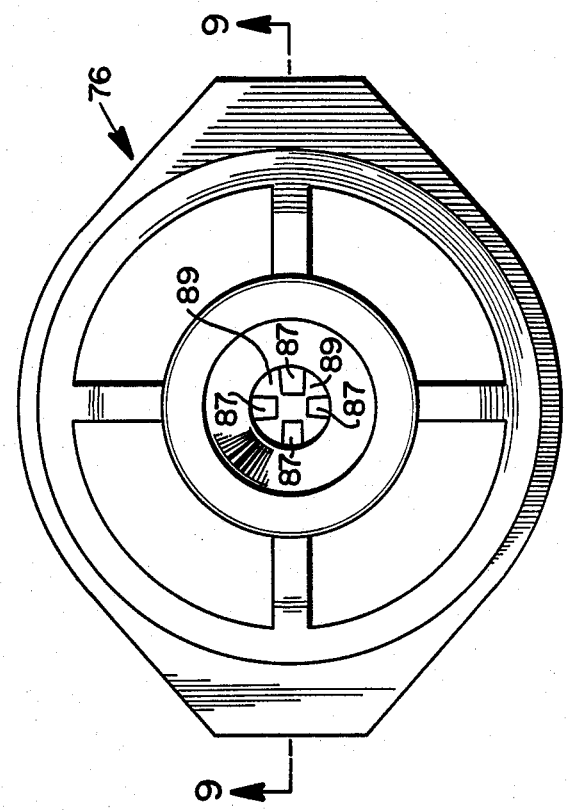

NEEDLE ASSEMBLY

BACKGROUND OF THE INVENTION

1. Field of the Invention:

The present invention relates to a needle assembly and more particularly concerns an improved needle assembly for use with hypodermic syringes or other fluid transferring devices.

2. Description of the Prior Art:

Hypodermic needle assemblies, including a cannula and a hub, are oftentimes removably attached to syringes for performing a variety of tasks such as the administration of medication to patients and into devices, and for the withdrawing of fluid samples from patients and from fluid sources. In some cases the cannula is attached directly to the syringe barrel, thus eliminating the hub. Further, many fluid delivery tube sets, fittings and stop cocks have a standard luer or locking luer fitting so that needle assemblies may be used in a variety of drug delivery systems such as in intravenous (IV) therapy and in a variety of fluid handling laboratory setups. Needle assemblies are also used for blood collection and in industrial applications such as dispensing liquids.

A fundamental requirement for a cannula and hub assembly, and an assembly of a cannula and a syringe barrel, is that the resulting assembly be capable of holding the cannula so that it is firmly connected to the hub or syringe and cannot be easily pulled therefrom. Also, the cannula should be substantially aligned with the longitudinal axis of the hub or syringe barrel and not projecting angularly therefrom. Proper alignment between the cannula and the hub and/or syringe barrel is important to help the user properly guide the cannula into the patient's body during injection and to avoid accidental skin punctures after injection when reshielding the cannula. Further, the manufacturing process used should not create particles or debris in the lumen of the cannula which may later be injected into the patient presenting a potential health hazard.

From a manufacturing process point of view, it can be undesirable to provide a hub which has a cannula reception bore which is smaller than the outside diameter of the cannula. It is believed that, unless dimensional tolerances are carefully controlled, forcing the hollow cannula through a smaller bore, especially with a plastic hub, allows the fine edges of the cannula to potentially skive plastic material from the hub inside diameter wherein this material may be later injected into the patient. Also, the forced assembly of a cannula and hub presents quality problems during mass production because of the difficulty in controlling the forces involved. This is especially true when many cannula hub assemblies are being processed at the same time. Also, the forceful assembly of these components eliminates the possibility of using prcesses wherein the cannula is later removed from the hub during the manufacturing process for application of adhesive and subsequently reinstalled into the hub.

Cannula and hub assemblies wherein adhesive is used to bond the cannula to the hub may also present problems where the hub structure allows the adhesive to nearly contact the open proximal end of the cannula because if the adhesive flows into the cannula lumen there is a potential for clogging the cannula. Also, attempting to apply adhesive deeply into the space between hub and loosely fitting cannula presents quality control problems because the process becomes sensitive to the viscosity, temperature and delivery pressure of the adhesive.

U.S. Pat. No. 3,186,408 to Jacob teaches a cannula and hub assembly wherein the cannula mounting portion of the hub has a greater inside diameter than the outside diameter of the cannula so that the space therebetween can be filled with adhesive. Jacob does not appear to provide structure to assure the alignment of the cannula with the hub. The Jacob design, theoretically, allows the adhesive to cover all of that portion of the cannula which is within the hub and potentially, in spite of statementss to the contrary, to enter the lumen of the cannula.

U.S. Pat. No. 3,472,227 to Burke teaches an improved cannula hub assembly wherein the proximal end of the cannula is physically engaged in the hub, in an interference or frictional fit, to maintain the relative position between the cannula and the hub. This interference would appear to prevent adhesive from passing through to the proximal end of the cannula. Although Burke provides structure to prevent the undesirable entry of adhesive into the cannula, the structure of Burke does not eliminate the potential for skiving hub material into the cannula lumen, and also requires the apparent forceful engagement of the cannula and the hub.

Burke, in U.S. Pat. No. 3 523,533, teaches a three-piece needle hub assembly which has a snap-in limit stop provided to contact the proximal end of the cannula while distally placed inwardly positioned ribs engage the cannula upon insertion. After assembly, adhesive is apparently injected between the ribs to fill the cavity in the hub. Here, Burke's design allows potential for skiving of hub material and provides potential for adhesive to enter the proximal end of the cannula Further, the additional snap-in limit stop adds to the complexity of the cannula hub assembly and increases the number of dimensional tolerances which can negatively affect the alignment of the cannula and the hub.

Burke, in U.S. Pat. No. 3,523,532 teaches another three-piece cannula and hub assembly which is functionally similar to the above-mentioned U.S. Pat. No. 3,523,532 to Burke, except that the third component is snapped in from the distal end of the hub rather than from the proximal end. Here again, there is the potential for skiving hub material into the lumen, and also potential for entry of the adhesive into the lumen of the cannula.

U.S. Pat. No. 3,430,627 to Kitaj illustrates a typical cannula syringe tip assembly wherein the syringe tip contains a bore which is larger than the outside diameter of the cannula providing a space for adhesive to be introduced. The structure illustrated in the Kitaj patent does not provide structure for the alignment of the cannula with the syringe barrel and does not appear to eliminate the possibility of adhesive entering the proximal end of the cannula.

The prior rat teaches structures for producing a cannula and hub assembly which, in many cases, provides improved retention of the cannula to the hub. However, there is still a need for a simple, straightforward, reliable, easily fabricated needle assembly which provides structure for aligning the cannula and the hub without using an interference fit which can potentially produce foreign particles through skiving during assembly, and also provide an area for adhesive to bond the cannula to the hub which is remote from the proximal end of the cannula to reduce the potential of adhesive entering the cannula lumen. Further, it is desirable to provide a cannula hub structure wherein the adhesive is concentrated at one portion of the hub rather than distributed throughout the hub needle interface so that the adhesive is more accessible for curing techniques such as ultraviolet (UV) curing.

SUMMARY OF THE INVENTION

The needle assembly of the present invention comprises a cannula having a lumen therethrough along its longitudinal axis and a hub having a distal end, a proximal end and a passageway therethrough defining a hub longitudinal axis. The cannula is positioned partially within the hub projecting outwardly from the distal end of the hub so that the lumen and the passageway are in fluid communication. The proximal end of the hub is adapted to engage and become in fluid communication with fluid transfer apparatus. Holding means is provided at the distal end of the hub for independently preventing removal of the cannula from the hub. Positioning means, adjacent to and independent from the holding means, contains a portion of said cannula for limiting angular misalignment between the cannula longitudinal axis and the hub longitudinal axis and for limiting the length of the cannula in the passageway without preventing the removal of the cannula from the hub.

In accordance with another embodiment of the present invention, a needle assembly includes an elongate cannula having a first end, an opposite end portion and a side wall therebetween. This cannula has a lumen therethrough defining a cannula longitudinal axis. A hub having a proximal end for engaging fluid transfer apparatus, a distal end and a passageway therethrough defining a hub longitudinal axis is provided. The passageway includes an enlarged first portion at the distal end, a second portion adjacent to the first portion and a third portion adjacent to the proximal end wherein the first portion, the second portion and the third portion are in fluid communication. The cannula is positioned in the hub so that the opposite end portion of the cannula is within the second portion of the hub and the first end projects outwardly from the distal end of the hub. The second portion has a distally located positioning edge and a proximally located inclined positioning surface and the portion of the passageway between the positioning edge and the distal most portion of the positioning surface is larger in diameter than the cannula. The positioning surface tapers inwardly and proximally so that the passageway at the proximal end of the second portion is smaller in diameter than the cannula and contact between the opposite end portion of the cannula and the positioning surface prevents the cannula from moving proximally therefrom. Angular misalignment of the cannula longitudinal axis and the hub longitudinal axis is limited by contact between the cannula side wall and the positioning edge and contact between the cannula opposite end portion and the positioning surface. A quantity of adhesive is substantially in the volume described by the first portion and that portion of the cannula side wall within the first portion is provided for holding the cannula in a fixed relationship with respect to the hub.

BRIEF DESCRIPTION OF THE DRAWINGS

FIG. 8 is an enlarged top plan view of another alternative embodiment of the hub of the present invention showing the individual cannula positioning surfaces; and FIG. 9 is a cross-sectional view of the hub of FIG. 8 taken along line 9—9.

DETAILED DESCRIPTION

Figure 1:
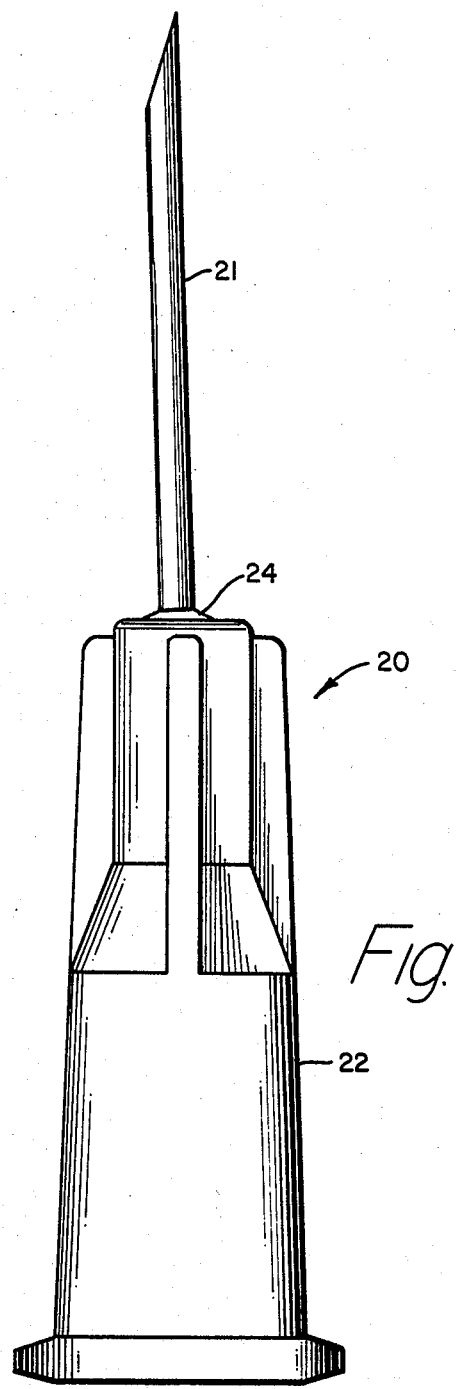
FIG. 1 is an enlarged side elevation view of the preferred needle assembly of the present invention.
Figure 2:
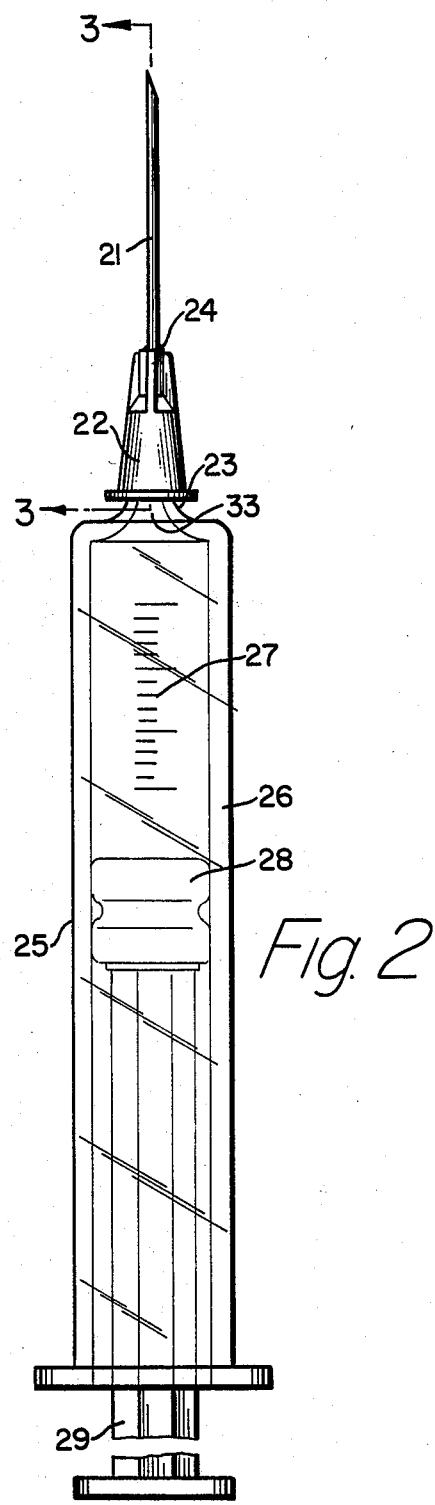
FIG. 2 is a side elevation view of the preferred needle assembly attached to a hypodermic syringe.
Figure 3:
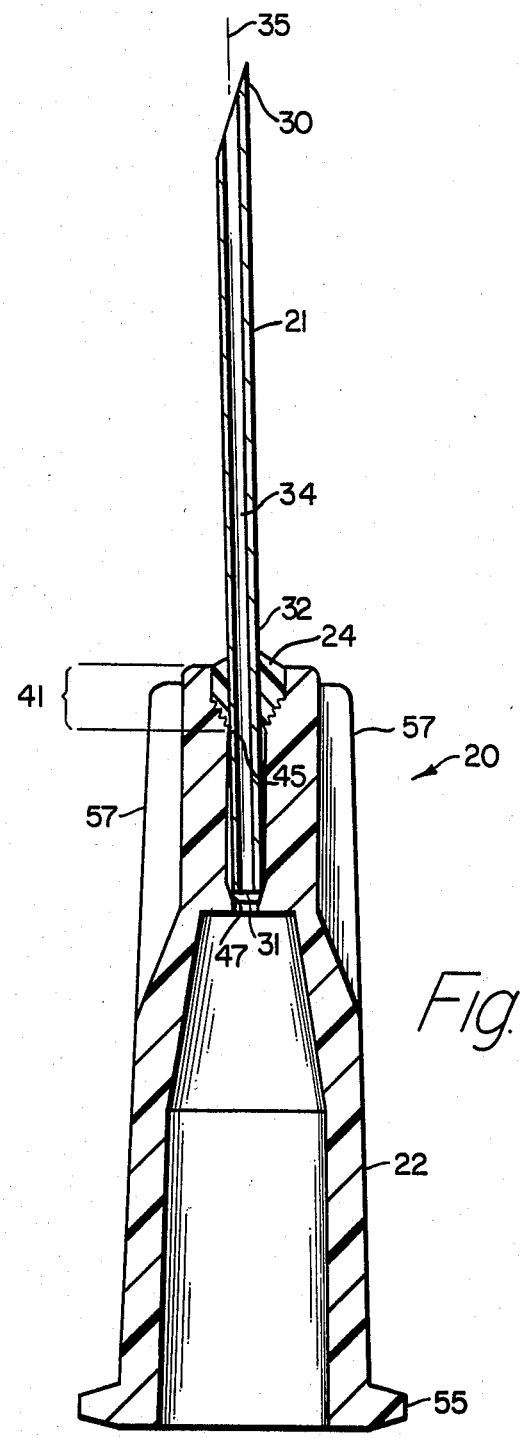
FIG. 3 is an enlarged cross-sectional view of the needle assembly of FIG. 2 taken along line 3—3 and shown without the syringe barrel.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-6, an improved needle assembly 20 includes an elongate cannula 21, a hub 22 and bonding material such as a quantity of adhesive 24, and is suitably used with hypodermic syringe 25 which typically includes a hollow barrel 26, a resilient stopper 28 and a rigid plunger rod 29.

Barrel 26 has an interior chamber 27 for retaining fluid. A tip 23 extends from the distal end of the barrel and contains a tip passageway 33 therethrough communicating with chamber 27. For purposes of the description of the present invention, the term "distal end" is meant to refer to the end furthest from the person holding the syringe, whereas the term "proximal end" is meant to refer to the end closest to holder of the syringe.

Stopper 28 is slidably positioned in fluid-tight engagement inside the barrel. Stopper 28 engages rigid plunger rod 29. In this embodiment, the stopper contains internal thread (not shown) which engages external thread (not shown) on the plunger rod. It will be apparent to one skilled in the art that numerous constructions can be used to join a stopper and a plunger rod and that the arrangement described above is exemplary of these many possibilities. Also, it is within the purview of this invention to include a one-piece plunger rod-stopper assembly. The plunger rod is accessible outside of the proximal end of the barrel and is provided to move the stopper along the barrel to force fluid into or out of the chamber through tip passageway 33. Specifically, the stopper is capable of moving fluid from the chamber through the passageway upon its movement toward the distal end of the barrel, and the stopper is capable of facilitating the drawing of fluid into the chamber through the tip passageway upon its movement away from the distal end of the barrel.

The cannula has a first end 30, an opposite end portion 31 and a side wall 32 therebetween. The first end is preferably sharpened if the cannula is to be used to inject fluid into the human body or through soft materials such as the pierceable septum of a medication vial or IV fitting. A lumen 34 extends through the cannula from the first end to the opposite end portion defining a cannula longitudinal axis 35. In this prefererd embodiment, cannula 21 has a circularly shaped cross section. Also, it is preferred that opposite end portion 31 be in a plane which is substantially perpendicular to the cannula longitudinal axis.

Figure 4:
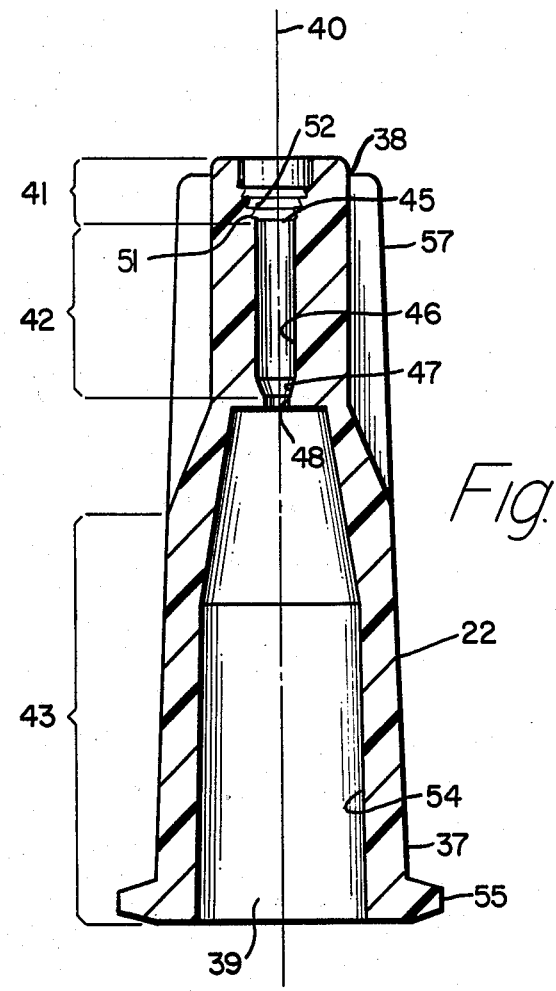
FIG. 4 is a cross-sectional veiw of the preferred hub of FIG. 3 shown without the cannula and the adhesive.

Hub 22 includes a proximal end 37, a distal end 38, and a passageway 39 therethrough defining a hub longitudinal axis 40. As will be explained in more detail hereinafter, proximal end 37 is adapted for removably engaging fluid transfer apparatus such as syringes, IV tubing fittings, laboratory fittings and the like. The passageway includes an enlarged first portion 41, a second portion 42 adjacent to the first portion and a third portion 43 adjacent to the proximal end of the hub. As best illustrated in FIG. 4, the first portion, second portion and third portion of the passageway are in fluid communication with each other. Second portion 42 includes a distally located, preferably circularly shaped, positioning edge 45 and a proximally located, preferably frusto-conically shaped, positioning surface 47 tapering inwardly in a proximal direction terminating at orifice 48 which is smaller in diameter than the outside diameter of the cannula. Positioning edge 45 and positioning surface 47 are separated by intermediate section 46 which is preferably cylindrically shaped and slightly larger in diameter than the cannula. It is preferred that both the positioning edge and the positioning surface be substantially centered along the hub longitudinal axis. For the purposes of the description of the present invention the term "positioning edge" is meant to include not only a relatively sharply defined edge, such as positioning edge 45 in FIG. 4, but also to include a surface formed by a radius or radii, such as positioning edge 85 in FIG. 9, wherein the outside surface cannula (not shown) would contact the surface tangentially.

Cannula 21 is positioned in the hub so that opposite end portion 31 is in the second portion of the passageway in contact with positioning surface 47, and cannula first end 30 projects outwardly from the distal end of the hub. Contact between opposite end portion 31 of the cannula and positioning surface 47 limits the depth to which the cannula enters the hub and resists further proximally directed movement of the cannula with respect to the hub.

A quantity of adhesive 24 is placed preferably within the volume described by the enlarged first portion and that portion of the cannula side wall within first portion 41 of the passageway. The adhesive is provided for holding the cannula in a fixed relationship with the hub and for preventing the cannula from being pulled out of the hub during normal use. The first portion is enlarged to provide an adequate volume to hold the adhesive. Alternating annular grooves 51 and inwardly facing annular ribs 52 provide structure for engaging the adhesive to further improve the joining of the adhesive to the first portion to, in turn, further increase the structural integrity of the needle assembly. As understood by one skilled in the art, there are numerous structures that are known to improve the holding power between adhesive and solid structure such as grooves alone, ribs alone, raised structure, recesses, and modified surface finishes, and that the alternating grooves and ribs shown herein are exemplary of these many possibilities.

Hub 22 preferably includes a tapered inside surface 54 which is sized and shaped to accept and removably engage tip 23 of known hypodermic syringe 25 so that there is fluid communication between interior chamber 27 of the syringe barrel through tip passageway 33 and hub passageway 39. Inside surface 54 should also accept and removably engage known IV tubing connectors and other known fluid flow fittings. External outwardly facing ribs 55 are provided to removably engage syringe tips or fluid flow fittings which contain a locking luer fitting (not shown). Longitudinal external ribs 57 provide an engagement surface for a rigid cannula shield (not shown) which is removably positioned over the cannula to protect it before use. It is important that cannula alignment with the hub be controlled so that the cannula tip is not damaged when the rigid shield is installed.

A cannula and hub assembly of the preferred embodiment using a 22 gauge cannula, 0.028 inch (0.71 mm) outside diameter preferably has a first portion having a maximum diameter, at the distal end of the hub, of approximately 0.070 inch (1.78 mm) and a length of approximaty 0.070 inch (1.78 mm). The second portion is approximately 0.145 (3.7 mm) inch long with its intermediate portion having a diameter of about 0.031 inch (0.79 mm). The positioning surface wall would be at an acute angle of about 10° with respect to the hub longitudinal axis.

During assembly of the preferred needle assembly, the hub is oriented so that the distal end faces upwardly. A cannula is dropped or inserted, opposite end portion first, into the hub through the first portion and the second portion. It should be noted that the enlarged funnel shape of the first portion helps guide the cannula into the second portion. As previously noted, positioning surface 47 limits how far the cannula enters the passageway. Because positioning surface 47 is tapered inwardly, it tends to center the cannula causing lumen 34 to be in fluid communication with orifice 48. When the elongate cannula is in a vertical position, it has a tendency to fall to a horizontal position, however, its motion from the vertical is limited by positioning edge 45 in the hub. Accordingly, the maximum angular misalignment of cannula longitudinal axis 35 and hub longitudinal axis 40 is limited by contact between the cannula side wall and positioning edge 45 and contact between the opposite end portion of the cannula and support surface 47 of the hub.

Figures 5, 6:
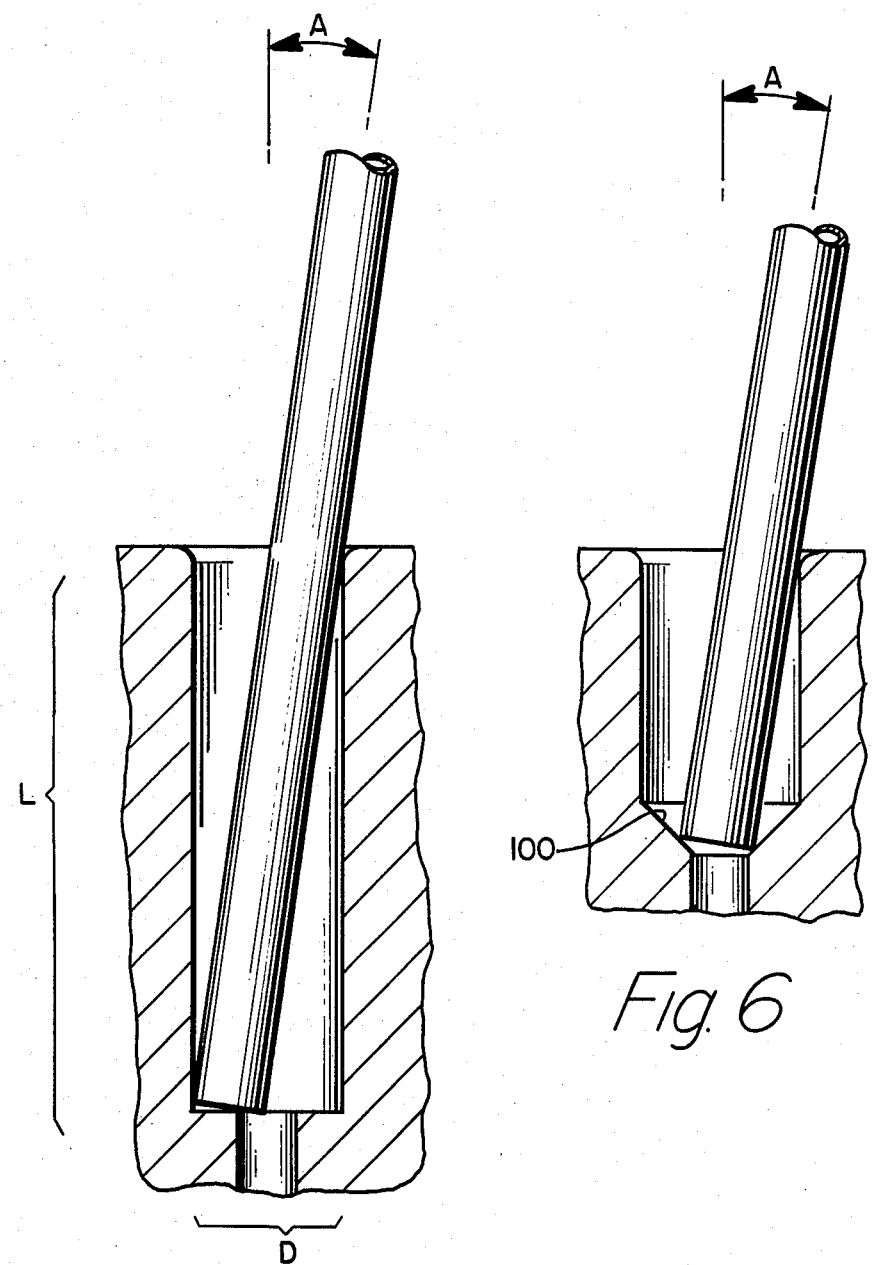
FIG. 5 is a partial cross-sectional view illustrating portions of a hub and a cannula to show how structure can be used to control hub and cannula alignment.
FIG. 6 is a partial cross-sectional view illustrating portions of a hub and a cannula to show how hub and cannula alignment are controlled in the present invention.

Reference to FIG. 5, which illustrates a portion of a hub passageway and a portion of a cannula, with the horizontal dimensions exaggerated shows haw a passageway in a hub may be used to control the angle between the hub passageway and the cannula. It can be seen that angle A, which represents the angle of misalignment between the longitudinal axis of the cannula and the longitudinal axis of the hub passageway, may be reduced by increasing the depth of the passageway L which contains the cannula or by reducing the diameter D of the cannula containing portion of the passageway. Increasing length L is an expensive solution because it requires an additional length of cannula and an additional length of hub which can result in a substantial cost increase when considered over millions of needle assemblies. Also, reduction of the diameter D is an expensive solution because it requires a tighter tolerance for the diameter dimension and also for the straightness of the passageway throughout the engaging length.

Another more cost effective method for controlling angle A is illustrated in FIG. 6. Here the length of the cannula and the length of the hub may be shortened while still maintaining substantially the same misalignment as provided for in FIG. 5. Or, in the alternative, the longer cannula and hub may be maintained while angle A is substantially reduced. The reduction of the value of angle A or the maintenance of the value of angle A while using shorter lengths of cannula and hub is accomplished by providing an inclined, preferably concentric, positioning surface 100 which causes the proximal end of the cannula to be substantially centered in the hub without reliance on the inside diameter of the passageway. The principals of FIG. 5 are used in all embodiments of the instant invention. Because the angular misalignment of the cannula with respect to the hub may be controlled with less cannula length and less hub length, it is now possible to provide a separate portion of the hub passageway for containing the adhesive and a separate portion for controlling the angle of the cannula without necessarily increasing the length of the hub. The advantages provided by this structure are important features of the present invention.

The present invention provides separate first portion 14 for substantially containing the adhesive. This portion is positioned at the distal-most end of the hub substantially reducing the probability of the adhesive flowing into the proximal end of the cannula lumen to block the lumen. Secondly, because second portion 42 is larger than the cannula outside diameter, inserting the cannula into the hub does not require a forcing action which may produce a skiving action between the proximal end of the cannula and the passageway to generate slivers or particles upon cannula insertion. It should be noted that the potential for adhesive entering the proximal end of the cannula lumen can be reduced by selecting the viscosity of the adhesive so that it will not readily flow in the space between the cannula outside diameter and the second portion, or by selecting an adhesive system wherein the adhesive will cure before it has time to flow into close proximity to the cannula lumen.

Also, the elimination of force to perform the initial assembly of cannula and hub reduces potential for damaging these components during assembly and eliminates the sensitive controls required to control the forced assembly of many needle assemblies at the same time. Further, the instant invention allows preliminary assembly of the cannula and hub wherein the cannula may be later removed in the process so that adhesive may be applied to the cannula side wall, and then the cannula may be reinserted into the hub. This type of assembly and adhesive application is not practical in cannula hub designs where an interference fit exists between the cannula and the hub. Also, the concentration of the adhesive at the distal end of the hub in the present invention allows the effective use of adhesives which must be exposed to specific conditions for curing, such as UV curable adhesive, because the adhesive is concentrated at a position where it may be readily exposed to the curing energy source. The hub of the present invention also facilitates the use of fast setting adhesives, such as hot melt adhesives, which must fill the volume provided in a relatively short time, before setting.

Thus, it is seen that the present invention provides structure for limiting misalignment between the cannula and the hub while reducing the potential for damage to the hub and cannula during assembly, reducing the generation of particles in the cannula lumen during assembly and reducing the potential for adhesive to enter the cannula lumen during assembly. This combination of improvements represents a substantial departure from the known prior art.

Figure 7:
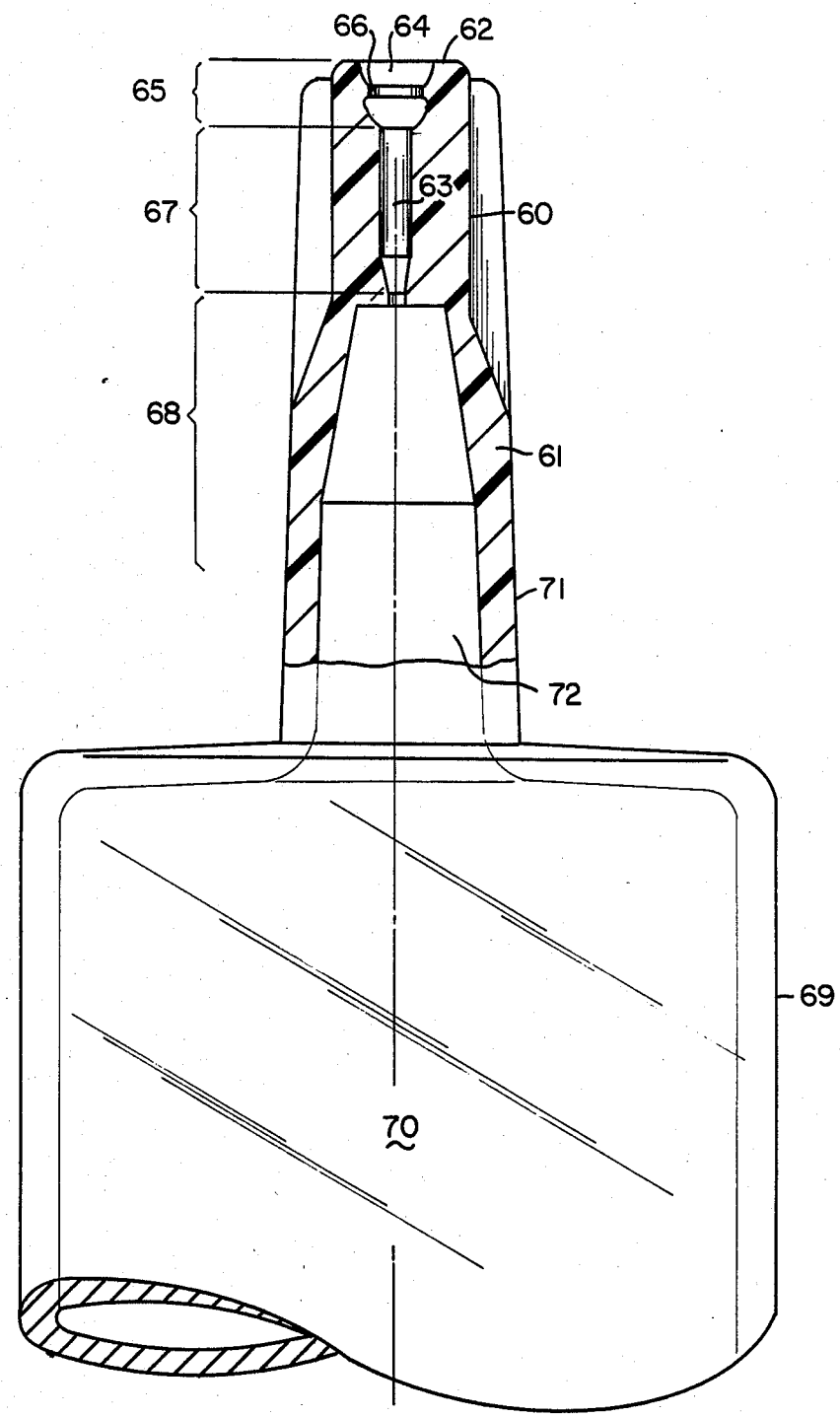
FIG. 7 is an enlarged partial cross-sectional view of an alternative embodiment of the hub of the present invention integrally attached to a syringe barrel.

Referring now to FIG. 7, an alternative embodiment of the instant invention includes a hub portion 60 having a proximal end 61, a distal end 62 and a passageway 64 therethrough. The passageway includes an enlarged first portion 65, a second portion 67 adjacent to the first portion and a third portion 68. The first portion is similar in function to the first portion described in conjunction with the previous embodiment. First portion 65 includes an annular inwardly projecting rib 66 in a plane transverse to hub longitudinal axis 63 for cooperating with the adhesive (not shown) to help prevent removal of the cannula (not shown) from the hub. The second portion is substantially identical in shape and function as the second portion described in conjunction with the previous embodiment. In this alternative embodiment, the proximal end of the hub portion is integrally connected to a preferably elongate syringe barrel 69 having a hollow chamber 70 for retaining fluids. A distal end 71 of the barrel includes a conduit 72 communicating with the chamber and passageway 64. This embodiment allows the elimination of a separate hub so that the cannula (not shown) may be attached directly to the hub portion which is integral with the syringe barrel proximal end.

Adverting to FIGS. 8 and 9, another alternative embodiment of the present invention includes a hub 76 having a proximal end 77, a distal end 78 and a passageway 79 therethrough defining a hub longitudinal axis 80. Proximal end 77 is adapted to engage fluid transfer apparatus such as syringes, IV tubing fittings, laboratory fittings and the like. The passageway includes an enlarged first portion 81, a second portion 82 adjacent to the first portion and a third portion 83 adjacent to the proximal end. Second portion 82 includes a distally located positioning edge 85 formed by a radius at the intersection with the first portion. The second portion also includes four proximally located, separate inclined positioning surfaces 87 located around the hub longitudinal axis. Each of the positioning surfaces is inclined at substantially the same angle with respect to the hub longitudinal axis. The positioning surfaces are tapered inwardly in a proximal direction terminating at opening 88 which is smaller than the outside diameter of the cannula (not shown). The first, second and third portions of the passageway of this embodiment perform the same functions as the respective first, second and third portions of the hub hereinabove described. However, the individual positioning surfaces have spaces 89 located therebetween. This structure allows the use of a cantilever-like positioning surface which is, by virtue of its structure, more flexible than a conically shaped positioning surface so that the individual positioning surfaces may flex independently to contact a cannula engaging them at a slight angle from the hub longitudinal axis. Spaces 89 allow gases displaced by adhesive (not shown) entering the first portion, during the assembly process, to flow longitudinally along the outside of the cannula and escape through spaces 89. It is preferred that there be at least three separate inclined positioning surfaces to properly center the cannual (not shown) in the third portion of the passageway.

In use, the needle assembly of the present invention may be attached to a hypodermic syringe which is then filled with liquid medication using known techniques. The syringe with needle assembly attached may then be used to inject the liquid medication into the patient's body, again, using known techniques. In the embodiment where the hub portion is integrally formed with the syringe barrel, the present invention may be used in the same manner described hereinabove except that it is not necessary to install the needle assembly onto the syringe barrel because the cannula is already attached to the syringe barrel.

The hub may be constructed of a wide variety of rigid material such as metals, plastics, ceramics and the like. Thermoplastic materials are preferred due to their low cost and proven compatability with many liquid medications. A wide variety of materials including metals and plastics may be used to fabricate a cannula. However, in most cases a medical grade stainless steel is preferred. A wide variety of adhesives such as hot melt adhesive, heat curable adhesive, UV curable adhesive and two-part epoxy are suitable for bonding the cannula to the hub. Heat curable epoxy manufactured by Amicon Corporation, Lexington, Mass. and sold under the name UNISET is preferred. It is preferred that all elements of the improved needle assembly be sterile when used. Accordingly, materials should be selected for compatability with the sterilization process being used.

Thus, the present invention provides a simple, straightforward, reliable, easily fabricated improved needle assembly which provides structure for aligning the cannula and the hub without using an interference fit which can produce foreign particles during the assembly process. The present invention also provides an area for the adhesive to bond the cannula to the hub which is remote from the proximal end of the cannula to reduce the potential for adhesive entering the cannula lumen prior to adhesive cure. Further, the adhesive in the present invention is concentrated at the distal end of the hub so that it is more accessible for curing techniques such as UV curing.

What is claimed is:

1. A needle assembly comprising:
   an elongate cannula having a first end an opposite end portion and a side wall therebetween, said cannula having a lumen therethrough defining a cannula longitudinal axis;
   hub means having a proximal end for engaging fluid transfer apparatus, a distal end and a passageway therethrough defining a hub longitudinal axis, said passageway having an enlarged first portion at said distal end, a second portion adjacent to said first portion and a third portion adjacent to said proximal end, said first portion said second portion and said third portion being in fluid communication, said cannula being positioned in said hub means so that said opposite end portion is within said second portion and said first end projects outwardly from said distal end of said hub means;
   said second portion having a distally located positioning edge and a proximally located inclined positioning surface, the portion of said passageway between said positioning edge and the distal most portion of said positioning surface being larger in a direction substantially perpendicular to said hub longitudinal axis than said cannula measured in a direction substantially perpendicular to said cannula longitudinal axis, said positioning surface tapering inwardly so that said passageway at the proximal end of said second portion is smaller than said cannula preventing said cannula from moving proximally therefrom whereby angular misalignment of said cannula longitudinal axis and said hub longitudinal axis being limited by contact between said cannula side wall and said positioning edge and contact between said cannula opposite end portion and said positioning surface; and
   bonding means in the volume described by said first portion and the portion of said cannula side wall within said first portion for holding said cannula in a fixed and immovable relationship with respect to said hub means.

2. The needle assembly of claim 1 wherein said cannula has a circularly-shaped cross section.

3. The needle assembly of claim 1 wherein said first end of said cannula has a sharpened surface.

4. The needle assembly of claim 1 wherein said positioning edge is circularly shaped and substantially centered on said hub longitudinal axis.

5. The needle assembly of claim 1 wherein said positioning surface is a frusto-conically shaped surface tapering toward said proximal end.

6. The needle assembly of claim 1 wherein said positioning surface includes a plurality separate inclined contact surfaces positioned around the said hub longitudinal axis, each of said contact surfaces inclined at substantially the same angle with respect to said hub longitudinal axis.

7. The needle assembly of claim 6 wherein said contact surfaces are spaced substantially equally distant with respect to each other around said hub longitudinal axis.

8. The needle assembly of claim 1 wherein said first portion includes an annular inwardly projecting rib in a plane transverse to said hub longitudinal axis for cooperating with said bonding means to help prevent removal of said cannula from said hub means.

9. The needle assembly of claim 1 wherein said first portion of the passageway includes an annular groove in said passageway in a plane transverse to said hub longitudinal axis for cooperating with said bonding means to help prevent removal of said cannula from said hub means.

10. The needle assembly of claim 1 wherein said first portion is substantially frusto-conically shaped and is larger in diameter at said distal end than at the intersection of said first portion and said second portion of said passageway.

11. The needle assembly of claim 1 wherein said third portion of said passageway and said proximal end of said hub means are adapted to engage the tapered tip of a hypodermic syringe barrel so that said passageway is in fluid communication with the interior of the barrel.

12. The needle assembly of claim 1 wherein said proximal end of said hub means is integrally connected with an elongate syringe barrel having a hollow chamber for retaining fluids a distal end of said barrel having a conduit therethrough communicating with said chamber, said conduit and said passageway being in fluid communication.

13. The needle assembly of claim 1 wherein said bonding means includes an adhesive selected from the group consisting of hot melt adhesive, heat curable adhesive, UV curable adhesive, and two-part epoxy.

14. The needle assembly of claim 1 wherein said hub means is made of thermoplastic material.

15. A needle assembly comprising:
- an elongate cannula having a first end, an opposite end portion and a side wall therebetewen, said cannula having a lumen therethrough defining a cannula longitudinal axis;
- a hub having a proximal end for engaging fluid transfer apparatus, a distal end and a passageway therethrough defining a hub longitudinal axis, said passageway having an enlarged first portion at said distal end, a second portion adjacent to said first portion and a third protion adjacent to said proximal end, said first portion, said second portion and said third portion being in fluid communication, said cannula being positioned in said hub so that said opposite end portion is within said second portion and said first end projects outwardly from said distal end of said hub, said second portion having a distally located positioning edge and a proximally located inclined positioning surface, the portion of said passageway between said positioning edge and the distal most portion of said positioning surface being larger in diameter than said cannula, said positioning surface tapering inwardly and proximally so that said passageway at the proximal end of said second portion is smaller in diameter than said cannula, contact between said opposite end portion and said positioning surface preventing said cannula from moving proximally therefrom, whereby angular misalignment of said cannula longitudinal axis and said hub longitudinal axis being limited by contact between said cannula side wall and said positioning edge and contact between said cannula opposite end portion and said positioning surface; and
- a quantity of adhesive in the volume described by said first portion and the portion of said cannula side wall within said first portion for holding said cannula in a fixed and immovable relationship with respect to said hub.

16. The needle assembly of claim 15 wherein said positioning surface is a frusto-conically shaped surface tapering toward said proximal end.

17. The needle assembly of claim 15 wherein said third portion and said proximal end are adapted to engage the tapered tip of a hypodermic syringe barrel so that said passageway is in fluid communication with the interior of the barrel.

18. The needle assembly of claim 15 wherein said proximal end of said hub is integrally connected with an elongate syringe barrel having a hollow chamber for retaining fluids, a distal end of said barrel having a conduit therethrough communicating with said chamber, said conduit and said passageway being in fluid communication.

19. The needle assembly of claim 15 wherein said adhesive is selected from the group consisting of hot melt adhesive, heat curable adhesive, UV curable adhesive, and two-part epoxy.

20. A syringe assembly comprising:
- a hollow barrel having a chamber for retaining fluid, a tip extending from a distal end of said barrel having a tip passageway therethrough communicating with said chamber;
- a stopper slidably positioned in fluid-tight engagement inside said barrel adapted to engage a plunger rod to facilitate its operation, said stopper capable of moving fluid from said chamber through said passageway upon its movement toward said distal end, said stopper capable of facilitating the drawing of fluid into said chamber through said passageway upon its movement away from said distal end;
- an elongate cannula having a first end, an opposite end portion and a side wall therebetween said cannula having a lumen therethrough defining a cannula longitudinal axis;
- a hub having a proximal end, a distal end and a passageway therethrough defining a hub longitudinal axis said passageway having an enlarged first portion at said distal end, a second portion adjacent to said first portion and a third portion adjacent to said proximal end, said first portion, said second portion and said third portion being in fluid communication, said cannula being positioned in said hub so that said opposite end portion is within said second portion and said first end projects outwardly from said distal end of said hub, said second portion having a distally located positioning edge and a proximally located inclined positioning surface, the portion of said passageway between said positioning edge and the distal most portion of said positioning surface being larger in a direction substantially perpendicular to said hub longitudinal axis than said cannula measured in a direction substantially perpendicular to said cannula longitudinal axis, said positioning surface tapering inwardly so that said passageway at the proximal end of said second portion is smaller than said cannula preventing said cannula from moving proximally therefrom whereby angular misalignment of said cannula longitudinal axis and said hub longitudinal axis being limited by contact between said cannula side wall and said positioning edge and contact between said cannula opposite end portion and said positioning surface;
- bonding means in the volume described by said first portion and the portion of said cannula side wall within said first portion for holding said cannula in a fixed and immovable relationship with respect to said hub and
- said tip being positioned in said third portion of said passageway so that said hub is removably engaged with said tip and said tip passageway is in fluid communication with said passageway in said hub.

* * * * *